United States Patent
Mathiowitz et al.

(10) Patent No.: US 6,511,749 B1
(45) Date of Patent: Jan. 28, 2003

(54) PREPARATION OF MULTIWALL POLYMERIC MICROCAPSULES FROM HYDROPHILIC POLYMERS

(75) Inventors: Edith Mathiowitz, Brookline, MA (US); Jules S. Jacob, Taunton, MA (US); Donald E. Chickering, III, Providence, RI (US); Kathleen Jo Pekarek, Midland, MI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 08/990,365

(22) Filed: Dec. 15, 1997

Related U.S. Application Data

(62) Division of application No. 08/478,103, filed on Jun. 7, 1995, now Pat. No. 5,985,354, which is a continuation-in-part of application No. 07/906,403, filed on Jul. 1, 1992, now Pat. No. 5,912,017, which is a continuation of application No. 07/045,840, filed on May 1, 1987, now Pat. No. 4,861,627.

(51) Int. Cl.[7] .......................... B32B 15/02; B32B 17/02; B32B 19/00; B32B 21/02
(52) U.S. Cl. ............................ 428/402.2; 428/402.21; 428/402.24; 428/403
(58) Field of Search ........................... 428/403, 402.21, 428/402.24, 402.2; 424/493, 496

(56) References Cited

U.S. PATENT DOCUMENTS

| 3,265,630 A | 8/1966 | Jensen |
| 3,523,906 A | 8/1970 | Vrancken et al. |
| 3,523,907 A | 8/1970 | Vrancken et al. |
| 3,627,693 A | 12/1971 | Scarpelli |
| 3,714,065 A | 1/1973 | Kitajima et al. |
| 3,755,558 A | 8/1973 | Scribner |
| 3,943,063 A | 3/1976 | Morishita et al. |
| 3,960,757 A | 6/1976 | Morishita et al. |
| 4,093,709 A | 6/1978 | Choi et al. |
| 4,138,344 A | 2/1979 | Choi et al. |

(List continued on next page.)

FOREIGN PATENT DOCUMENTS

| DE | 2030 604 | 1/1971 |
| WO | WO 90/11092 | 10/1990 |
| WO | WO 93/01286 | 1/1993 |

OTHER PUBLICATIONS

Albertsson & Tjerneld, *Methods in Enzymology*, 228:3–12 (Academic Press, New York 1994).

Albertsson, "Partition of Cell Particles and Macromolecules" (3d ed. Wiley (Interscience), New York 1986).

Bakan & Anderson, "Microencapsulation" in *The Theory and Practice of Industrial Pharmacy*, pp. 384–407 (Lea & Febiger, Philadelphia 1970).

(List continued on next page.)

*Primary Examiner*—Cynthia H. Kelly
*Assistant Examiner*—B. Shewareged
(74) *Attorney, Agent, or Firm*—Holland & Knight LLP

(57) ABSTRACT

Two or more hydrophilic polymers that are not soluble in each other at a particular concentration and temperature, but which have a positive spreading coefficient in solution, are used to form multi-layered polymeric microspheres. The multi-layer microspheres produced by the method are distinguished by extremely uniform dimensioned polymer layers and actual incorporation of a substance to be delivered into the polymer layers. In the preferred embodiment of the method, two polymers are dissolved in an aqueous solvent, the substance to be incorporated is dispersed or dissolved in the polymer solution, the mixture is suspended in an organic solvent or polymer/water mixture and stirred, and the solvent is slowly evaporated, creating microspheres with an inner core formed by one polymer and an outer layer formed by the second polymer.

7 Claims, 2 Drawing Sheets

U.S. PATENT DOCUMENTS

| | | | |
|---|---|---|---|
| 4,166,800 A | | 9/1979 | Fong |
| 4,180,606 A | | 12/1979 | Hance et al. |
| 4,187,194 A | | 2/1980 | Wellman et al. |
| 4,263,273 A | | 4/1981 | Appelgren et al. |
| 4,272,398 A | | 6/1981 | Jaffe |
| 4,389,330 A | | 6/1983 | Tice et al. |
| 4,479,911 A | | 10/1984 | Fong |
| 4,585,651 A | | 4/1986 | Beck et al. |
| 4,622,244 A | | 11/1986 | Lapka et al. |
| 4,637,905 A | | 1/1987 | Gardner |
| 4,675,189 A | | 6/1987 | Kent et al. |
| 4,756,907 A | | 7/1988 | Beck et al. |
| 4,792,598 A | | 12/1988 | Ziegast |
| 4,861,627 A | | 8/1989 | Mathiowitz et al. |
| 5,000,886 A | | 3/1991 | Lawter et al. |
| 5,407,609 A | | 4/1995 | Tice et al. |
| 5,912,017 A | * | 6/1999 | Mathiowitz et al. ........ 424/494 |

OTHER PUBLICATIONS

Gutcho, *Microcapsules and Microencapsulation Techniques* (Noyes Data Corp., Park Ridge, New Jersey, USA 1976).

Harkins, *The Physical Chemistry of Surface Films*, p. 23 (Reinhold Pub. Co., New York 1952).

Harris, et al., "Enzyme Purification Using Temperature Induced Phase Formation," *Bioseparation*, 2:237–246 (1991).

Hobbs, et al., "Effect of Interfacial Forces on Polymer Blend Morphologies", *Polymer*, 29:1598–1602 (1988).

Kirk–Othmer, *Encyclopedia of Chemical Technology* (3d ed.), vol. 15, Microencapsulation, pp. 470–493.

Kirk–Othmer, *Encyclopedia of Chemical Technology* (2 ed.), vol. 13 Microencapsulation, pp. 436–457.

Kokkoris, et al., "Yeast Cell Debris and Protein Partitioning in the Poly(ethylene glycol)–Poly(vinyl alcohol) Biphasiz System," *Biochem. Biophys. Acta*, 966:176–180 (1988).

Kondo, *Microsapsule Processing and Technology*, pp. 70–81 (Marcel Dekker, Inc., New York 1979).

Lu, et al., "Preparation of Benzoyl Detran and its Use in Aqueous Two–Phase Systems," *Bioseparation*, 2:247–255 (1991).

Sturesson, et al., "Partition of Macromolecules and Cell Particles . . . " in *Applied Biochem. & Biotechnol.*, (Weetzall, ed.) 26:281 (1990).

Szlag & Giuliano, "A Low Cost Aqueous Two–Phase System for Enzyme Extraction," *Biotechnol. Tech.*, 2(4):277–288 (1988).

Tjerneld, "New Polymers for Aqueous Two–Phase Systems," in *Separations Using Aqueous Phase Systems*, (Fisher & Sutherland, eds.), p. 429 (Plenum, New York 1989).

Walter, et al., eds, *Partitioning in Aqueous Two–Phase Systems* (Academic Press, Inc., London, England 1985).

\* cited by examiner

PREPARATION OF MULTIWALL POLYMERIC MICROCAPSULES FROM HYDROPHILIC POLYMERS

This application is a divisional of U.S. Ser. No. 08/478, 103, filed Jun. 07, 1995, issued as U.S. Pat. No. 5,985,354, which is a CIP of Ser. No. 07/906,403 issued as U.S. Pat. No. 5,912,017, which is a continuation of U.S. Ser. No. 07/045, 840, filed May 1, 1987, issued as U.S. Pat. No. 4,861,627.

BACKGROUND OF THE INVENTION

The present invention is a method for preparing multiwall polymer microspheres, particularly for use in controlled delivery systems.

This is a continuation-in-part of U.S. Ser. No. 07/906,403, filed Jul. 1, 1992, by Edith Mathiowitz and Robert Langer, which is a continuation-in-part of U.S. Ser. No. 07/045,840- entitled "Preparation of Multiwall Polymeric Microcapsules" filed May 1, 1987 by Edith Mathiowitz and Robert S. Langer, issued as U.S. Pat. No. 4,861,627 on Aug. 29, 1989.

Controlled delivery of substances, for example, drugs, insecticides, fertilizers, detergents, perfumes, and indicators, can be accomplished using a variety of processes. In one type of delivery system, a polymeric capsule is formed around or incorporating the substance to be delivered. The form and composition of the polymer or polymers determines the method that can be used to incorporate the substance, the environment in which the capsule can be used, and the type of substance which can be incorporated.

One process for preparing microspheres is a hot-melt technique. The melted polymer is mixed with the drug, and the mixture is suspended in a non-solvent where it is cooled and solidified. A major disadvantage of this process is that only low melting polymers can be used with thermolabile substances.

The solvent evaporation technique, disclosed, for example, by U.S. Pat. No. 3,523,906 to M. N. Vrancken and U.S. Pat. No. 3,960,757 to M. Morishita, has been used to prepare microspheres from biodegradable polymers, as reported in the literature and by H. Jaffe in U.S. Pat. No. 4,272,398. The procedure generally consists of dissolving a polymer in methylene chloride or other volatile solvents, dissolving or suspending a drug in the solution and emulsifying the resulting mixture in an aqueous phase containing an emulsifier. The solvent is evaporated to produce microspheres containing the substance to be incorporated. The technique of Morishita dissolves a hydrophobic polymer in an organic solvent which is poorly miscible with water and has a boiling point less than water. A substance is dissolved or mixed in the polymer solution, the solution is emulsified in an aqueous solution of a hydrophilic colloid or surface active agent, and the organic solvent is removed by evaporation. A major limitation of this method is that the solvents used can be harmful to biologically active material to be encapsulated.

Yet another method used to form microcapsules is phase separation. Essentially, a polymer is forced to precipitate around a core by addition of non-solvent or by addition of a second polymer which is incompatible with the first polymer.

A polymer coating can be added to spherical particles using a fluidized bed method. In this method, microspheres of one polymer or particles of the substance to be encapsulated are suspended in a vertical column by air flow. The polymer used for coating is dissolved in an appropriate solvent and sprayed down over the suspended particles. A uniform polymer coating may be obtained for particles larger than 50 μm. This method, however, is not appropriate for water-soluble polymers due to the time required for water evaporation.

U.S. Pat. No. 4,861,627 to Mathiowitz, describes a method for making polymeric microspheres with a polymeric core made of a first polymer, a uniform coating layer made of a second polymer, and a substance incorporated in at least one of the polymers. The first and second polymer are immiscible in each other, and separate into distinct phases when dissolved in appropriate solvents or when melted together. The interfacial tension of the polymers causes one polymer to engulf the other polymer, resulting in microspheres with a core of one polymer, and a uniform coating of the second polymer. The microspheres are made from polymers that are soluble in a volatile organic solvent.

While all of these methods are useful in making microspheres or microcapsules for controlled delivery, they have certain disadvantages. The coating method described in U.S. Pat. No. 4,861,627 provides microspheres with uniform layers, but is not applicable to hydrophilic polymers that are not soluble in volatile organic solvents. Other coating methods, which are applicable to hydrophilic polymers, do not always yield uniform polymer layers. The best one can do at present is to dip microspheres formed of one polymer into a bath of a second polymer (pan coating). However, the coatings tend to be non-uniform both with respect to coverage and to thickness. This can be fatal to a system for controlled delivery, as in controlled drug delivery systems requiring linear release of the drug as the polymer degrades in vivo. Further, many of these methods require multiple steps, with increasing quality control problems at each stage. The final yield is frequently low.

It is therefore an object of the present invention to provide a one step method for manufacturing delivery systems consisting of two or more hydrophilic polymers in microcapsule form.

It is another object of the present invention to provide a method for making polymeric delivery devices where substances, in particle form if solids, or live cells, can be incorporated directly into polymers and which can be conducted at relatively low temperatures to avoid damaging any thermolabile substances to be incorporated.

SUMMARY OF THE INVENTION

A single step method for preparing multilayer polymeric drug, protein, or cell delivery devices from two or more hydrophilic polymers is disclosed. Any two or more different biodegradable, or non-degradable, water soluble polymers which are not soluble in each other at a particular concentration as dictated by their phase diagrams may be used. The multilayer microcapsules produced by the method have uniformly dimensioned layers of polymer and can incorporate a range of substances including biologically active agents such as drugs or cells, or diagnostic agents such as dyes.

In the preferred embodiment, two hydrophilic polymers are dissolved in an aqueous solution, a substance to be incorporated is dispersed or dissolved in the polymer solution, the mixture is suspended in a continuous phase, and the solvent is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

In another embodiment, two or more hydrophilic polymers are dissolved in mixtures of organic and aqueous solutions and then mixed together. By selecting the appropriate solvents and polymers, the two solutions will not be soluble in each other and will result in a suspension or emulsion. This insoluble mixture can then be suspended in yet another continuous phase, in which neither polymer is soluble, and the solvents are removed by evaporation.

In another embodiment, two hydrophilic polymers that gel upon a change in temperature are separately dissolved to form two polymer solutions. These solutions are mixed and phase separated so that one layer engulfs the other, then the temperature is altered to gel one of the polymers. Optionally, the temperature can be altered to gel the second polymer. In some embodiments, there is no need to dry the resulting microspheres, particularly when cells are encapsulated.

In another embodiment, polymers are selected that can be ionically or covalently cross-linked, or cross-linked by heating. Two polymer solutions are mixed and phase separated so that one polymer engulfs the other, then one or both of the polymers are cross-linked by adding a cross linking agent, for example, ions to effect ionic crosslinking, glutaraldehyde to effect chemical crosslinking with functional groups such as amine groups, or free-radical initiation effected by azobisisobutyronitrile (AIBN) or t-butyl peroxide, by photoinitiators active in the ultraviolet (UV) region, such as benzoin ethyl ether, or photoinitiators active in visible light to crosslink free-radical polymerizable groups, such as carbon-carbon double bonds.

In a further embodiment, solvents in polymer solutions are evaporated rapidly to produce multiple spheres of a first hydrophilic polymer within a layer of a second hydrophilic polymer. The rate of evaporation can be varied to form a core of the first polymer and a coating of the second polymer, or multiple spheres of a first polymer within a layer of the second polymer.

Important parameters for producing multi-layered microcapsules of the desired composition are: the selection of the hydrophilic polymers, including the purity and the molecular weights of the polymers, the solvent, the solubility and concentration of the polymers in the solvent, the selection and composition of the non-solvent, including adding an emulsifier to the non-solvent, the processing temperature, the rate of solvent evaporation, the rate of mixing, the physical and chemical properties of the substance to be incorporated, and ionic composition of the solvent (i.e., salt concentration). The optimum conditions can be determined empirically by one skilled in the art by measuring the surface tension or interfacial tension of the polymers under the processing conditions.

Examples demonstrate the production of multilayered microcapsules composed of polyethylene glycol and dextran, and gelatin and agarose.

DETAILED DESCRIPTION OF THE INVENTION

Figure 1:
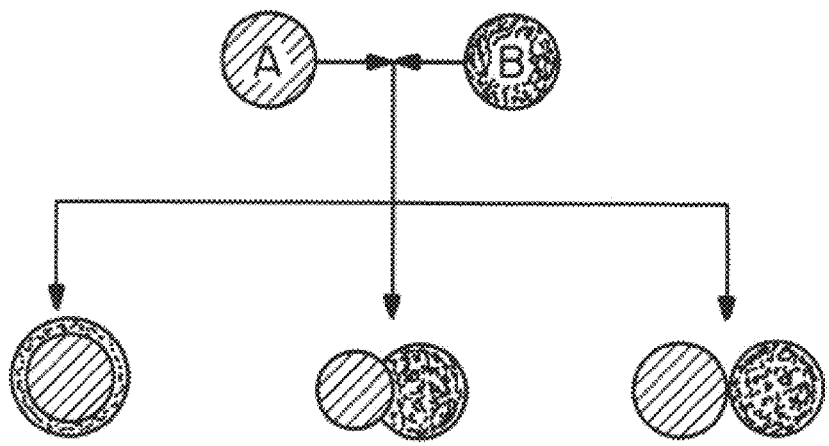
FIG. 1 is a schematic illustration of microspheres in which one polymer completely engulfs another polymer (lower left), one polymer partially engulfs another polymer (lower center), and neither polymer phase engulfs the other (lower right).

Microcapsules including a core of a first hydrophilic polymer and a coating of a second hydrophilic polymer and methods of forming the microcapsules are disclosed. In one embodiment, a substantially uniform coating of the second polymer may be obtained.

The method of the present invention is described in detail as follows.

I. COMPONENTS.

Polymer Selection

Polymers are selected on the basis of their physical and chemical properties, especially their degradation characteristics in vivo when used in biomedical applications. Polymers that are approved by the FDA as food ingredients are preferred for food applications and those which are approved for medical applications are preferred for medical applications. Factors which must be taken into consideration in the selection of the polymers include the purity of the polymers, their molecular weight, and their solubility in aqueous and aqueous/organic solutions. Further, the polymers must be immiscible in each other.

The polymers used in the method are preferably hydrophilic polymers. As defined herein, hydrophilic polymers are those which are soluble in water or mixtures of water and some polar organic solvents, such as low molecular weight alcohols, acetone, dimethylformamide, dimethyl sulfoxide, dioxane, acetonitrile and tetrahydrofuran. The polar organic solvent is preferably present at a concentration of about 0 to 50% by volume.

As used herein, "water-soluble" means that the entire polymer must be completely soluble in aqueous or aqueous/organic solutions, such as buffered saline or buffered saline with small amounts of added organic solvents as cosolvents.

Examples of water-soluble polymers include polyamines having amine groups on either the polymer backbone or the polymer side chains, such as poly-L-lysine and other positively charged polyamino acids of natural or synthetic amino acids or mixtures of amino acids, including poly(D-lysine), poly(ornithine), poly(arginine), and poly(histidine), and nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylaminopropyltrimethyl ammonium chloride), poly(ethyloxazoline), poly(N-vinyl pyrrolidone), and neutral poly(amino acids) such as poly(serine), poly(threonine), and poly(glutamine).

Other suitable polymers include naturally occurring proteins, such as gelatin, bovine serum albumin, and ovalbumin, as well as complex sugars, such as hyaluronic acid, starches and agarose. The polymer can be any biocompatible water-soluble polyelectrolyte polymer. In one embodiment, a polycationic polymer, for example, any polymer having protonated heterocycles attached as pendant groups, can be utilized.

Hydrophilic polymers also include poly(oxyalkylene oxides) such as poly(ethylene oxide), poly(vinyl alcohol), natural or synthetic polysaccharides and polysaccharide derivatives such as alginate, chitosan, dextran, water soluble cellulose derivatives such as hydroxy ethyl cellulose and carboxymethylcellulose, poly(hydroxyethyl acrylate), poly (hydroxy ethylmethacrylate), and polyacrylamides such as isopropylacrylamide. As used herein "derivatives" include polymers having substitutions, additions of chemical groups, for example, alkyl, alkylene, hydroxylations, oxidations and other modifications routinely made by those skilled in the art.

Two-phase aqueous systems have been widely used to purify complex mixtures of bioactive agents. A list of polymers commonly used in aqueous two phase systems, as reported in Albertsson and Tjerneld, Volume 228, *Methods in Enzymology* (Academic Press, New York), 1994, page 4, is shown in Table 1. Hydrophilic polymers which may be used to form microspheres include those listed in Table 1.

TABLE 1

| Aqueous Two Phase Systems | Refs. |
|---|---|
| Polymer-polymer Nonionic | |
| Dextran-poly(ethylene glycol) (PEG) | a |
| Dextran-poly(ethylene glycol propylene glycol) copolymer (Ucon) | b |
| Dextran-poly(vinyl alcohol) (PVA) | a |
| Dextran-ethylhydroxyethyl cellulose | c |
| Dextran-benzoyldextran | d |
| Dextran-hydroxypropyl dextran | a |
| Dextran-Ficoll | a |
| Dextran-polyvinylpyrrolidone (PVP) | a |
| Benzoyldextran-PEG | d |
| Hydroxypropyl starch-PEG | e |
| PVA-PEG | c,f |
| Maltodextrin-PEG | g |
| Pullulan-PEG | h |
| Poly(vinyl methyl ether)-PEG | i |
| Ionic | |
| Dextran sulfate-PEG | a |
| Carboxymethyl dextran-PEG | a |
| Dextran sulfate-poly(styrene sulfonate) | j |
| Dextran sulfate-DEAE-dextran | a |
| PVA-acrylic copolymers | k |
| Poly(acrylic acid)-PEG | l |
| Poly(acrylamide)-PVP | l |
| Salt-polymer | |
| Potassium phosphate-PEG | a |
| Ammonium sulfate-PEG | a |
| Potassium citrate-PEG | m |
| Magnesium sulfate-PEG | a | a P.A. Albertsson, "Partition of Cell Particles and Macromolecules," 3rd Fd. Wiley (Interscience), New York, 1986.
b P.A. Harris, G. Karlstrom, and F Tjerneld, Bioseparation, 2:237 (1991).
c F. Tjemeld, in "Separations Using Aqueous Phase Systems" (D. Fisher and I.A. Sutherland, eds.), p. 429, Plenum, New York, 1989.
d M. Lu, F. Tjerneld, G. Johannsson, and P.A. Albertson, Bioseparation, 2:247 (1991).
e S. Sturesson, F. Tjerneld, and G. Johansson, Appl. Biochem, Biotechnol 26:281 (1990).
f A. Kokkoris, J.B. Blair, and J.A. Shaeiwitz, Biochim. Biophys. Acta, 966:176 (1988).
g D.C. Szlag and K.A. Giuliano, Biotechnol. Tech., 2:277 (1988).

The systems are grouped according to nonionic-, ionic- and salt-polymer interactions. The variables that must be controlled when preparing two-phase aqueous systems include: polymer concentration and molecular weight, ionic composition, temperature, time allowed for separation and interfacial tension. The interfacial tension is directly affected by the polymer concentration. As an example, the interfacial tension of the PEG-dextan system can vary from 0.0001 to 0.1 mN m$^{-1}$ by increasing the concentration of the components.

Preferred biodegradable polymers include zein, bovine serum albumin, human serum albumin and synthetic copolymers of hydrophilic and hydrophobic polymers, such as PEG-PLGA copolymers. PLGA is defined as a copolymer of polyl-lactic acid and polyglycolic acid.

The polymers are either liquid at room temperature or can be liquified, for example, by melting the polymers or by dissolving the polymers in a solvent. The most important criteria for determining which polymer systems will form multilayer microspheres is the interfacial tension of the liquified polymers and the spreading coefficient for the polymer system. Interfacial tension can be measured, calculated from measured surface tension or determined from the published literature. The spreading coefficient of the polymer system is calculated from the interfacial tension. When the spreading coefficient is positive, one polymer will engulf the other.

The theory by which one can determine whether one polymer will completely engulf the other polymer by determining the surface and/or interfacial tension of the polymers in solution is discussed in detail below.

Mixing of the Polymer Solutions with the Substance to be Incorporated

The polymers can be combined with the substance to be incorporated in either of two ways. In one method, each polymer is dissolved or melted separately and the solutions combined. In the second, both polymers are simultaneously dissolved in one solvent or melted together. The ultimate dispersion of the substance within the polymeric microspheres is determined in part by the method of dissolution and combination. The substance to be incorporated can be added directly to one or both of the polymer solutions or to the mixture.

Elements of protein partitioning theory originally developed to separate various parts of cells from each other can be adapted to load one layer or another of a multi-layered polymer microsphere with a particular protein. The partitioning coefficient is dependent upon the properties of the protein itself and of the two phase separated polymers. For each protein, its partitioning between the polymers can be altered by changing certain properties of the polymers. By varying the pH, ionic composition, or temperature of the system, and/or the molecular weight and concentration of the polymers, the partitioning coefficient of the protein can be altered to achieve preferential loading of a particular polymer layer. For each system, the exact conditions for encapsulation must be determined experimentally from determined partitioning coefficients or from those reported in the literature. "Partitioning in Aqueous Two-Phase Systems," edited by Harry Walter, Donald E. Brooks, and Derek Fisher, Academic Press, Inc. (London, England), 1985.

The polymers are mixed together using conventional means such as an overhead stirring device, magnetic stirrer or agitation. The rate of stirring has an effect on the formation of the polymer layers and may be optimized for each polymer-solvent mixture.

Spreading Coefficient Calculation

The tendency of a liquid to spontaneously spread across a solid or liquid substrate can be expressed in terms of the surface and interfacial tensions of the components using Harkin's equation, described by W.D. Harkin, "The Physical Chemistry of Surface Films", page 23 (Reinhold Pub. Co., New York 1952).

$$\text{a. lambda}_{ij} = \text{gamma}_j - \text{gamma}_i - \text{gamma}_{ij} \tag{1}$$

where gamma$_j$ and gamma$_i$ are the surface tensions of the substrate and the liquid respectively, gamma$_{ij}$ is the interfacial tension of the substrate and liquid, and lambda$_{ij}$ is the spreading coefficient of liquid i on substrate j. Spreading is predicted to occur only for positive values of lambda.

Harkin's equation can be rewritten for a system in which two dissimilar phases are dispersed within a third, by substituting the appropriate interfacial tensions for the surface tension values in equation 1:

b. lambda$_{31}$=gamma$_{12}$−gamma$_{32}$−gamma$_{13}$   (2)

In this case, lambda$_{31}$ is the spreading coefficient for component 3 on component 1 (conversely, lambda$_{13}$ is the spreading coefficient for component 1 on component 3) and describes the physical situation in which the ability of one dispersed component to displace the matrix from the surface of a second component is considered. In an analogy with equation (1), envelope formation will be observed when lambda values are positive; but when lambda$_{31}$ and lambda$_{13}$ are both negative the dispersed phases will remain separated. Equation 2 can also be used to predict the behavior of polymer blends, using the method of S. Y. Hobbs, M. E. J. Dekkers and V. H. Watkins, in Polymer, Vol. 29, 1598-1602, (1988), and references cited therein, if the interfacial tension for various polymers are known.

Polymeric Solutions or Liquids.

The same equations can be applied when two immiscible liquid drops, designated as phase 1 and 3, suspended in a third immiscible liquid, phase 2, are brought into contact. The resulting equilibrium configuration is readily predicted from the interfacial tension and the spreading coefficients. Three cases can be envisioned, as shown schematically in FIG. 1:

a) polymer A completely engulfing polymer B, or vice versa b) polymer B partially engulfmg polymer A, or vice versa, and c) both polymer phases non-engulfmg.

Based on this theory, it is possible to measure the interfacial tension, or calculate the interfacial tension based on measurements of the surface tension of the polymers in solution, and predict which polymer-solvent systems will yield multilayered microspheres.

The surface tension can be measured using techniques known to those skilled in the art. For example, one can use a surface tensiometer, which employs the du Nouy ring method and consists of a platinum ring of known diameter which is placed in the polymer solution, then slowly pulled vertically. The ring attaches to the surface of the liquid and resists detaching from the liquid. The force required to detach the ring from the surface of the liquid is measured and noted as apparent surface tension. This is multiplied by a correction factor, to determine the real surface tension.

Interfacial tension between liquids is measured similarly. Two liquids with different densities are carefully placed in a vessel to avoid mixing. The platinum ring is slowly inserted until it is well inside the lower liquid. The ring is lightly shaken to ensure that it is devoid of the top layer liquid, using caution so as to not mix the liquids, especially at the interface. The same procedure for determining surface tension is then followed, pulling the ring vertically until it breaks the surface of the bottom liquid and enters the liquid on the top.

Selection of the Aqueous or Aqueous Organic Solvents

The solvent system must be chosen in conjunction with the polymers so that the polymers to be incorporated into the microcapsules will initially go into aqueous solution and then separate into distinct phases, with one polymer being engulfed by another. Polymers can be dissolved in water, or an aqueous/organic solvent which includes a mixture of water and a polar organic solvent. The choice of solvent will depend on the substance to be incorporated into the polymers since some solvent systems may have a detrimental effect on the biological activity of the substance.

The aqueous/organic solutions may include a mixture of water and a preferred concentration of between about 0 and 50% by volume of a polar organic solvent. Suitable solvents include but are not limited to ketones such as acetone, ethers such as tetrahydrofuran, dibutyl ether and dimethylsulfoxide, alkanamides such as dimethylformamide, and low molecular weight alcohols such as methanol, ethanol, isopropanol and propanol. Other suitable solvents include dioxane, acetonitrile and glycerol.

Selection of the Substance to be Incorporated

Examples of substances which can be incorporated include drugs, fertilizers, insecticides, chemical indicators or dyes, chemical reactants, imaging contrast agents such as air and carbon dioxide, magnetic and radioactive compound, and scents or flavorings.

Biologically active substances that can be incorporated include proteins, carbohydrates, nucleic acids, and inorganic and organic, biologically active molecules. Specific examples include enzymes, vaccines, antibiotics, antineoplastic agents, anesthetics, hormones, angiogenic agents, antibodies, neurotransmitters, psychoactive drugs, drugs affecting reproductive organs, and antisense oligonucleotides.

The substance to be incorporated must not be adversely affected by the polymer, polymer solvent or the temperature at which solvent evaporation or gelation occurs. The substance is preferably provided in solution or in a particle size small enough to avoid "channeling" within the polymer, although it can also be provided in a suspension, or in the case of gases, can be provided by sonicating or aerating the polymer solution in the presence of a gas to be encapsulated. Particle sizes are preferably in the range of 50 microns or less.

A surface active agent can be added in a range of between 0 and 50% surface active agent by volume of the second solution. Useful surface active agents include polyvinyl alcohol, gelatin, and other surfactants and emulsifiers known to those skilled in the art.

II. MICROSPHERE PREPARATION AND CHARACTERIZATION.

Multi-layer polymeric microcapsule delivery systems may be prepared which include a substance, such as a bioactive agent in the polymeric layers. In one embodiment, first and second polymers are dissolved in an aqueous solution, the substance to be encapsulated is dispersed or dissolved in the polymer solution, and the mixture is suspended in a third solution which can be either an organic solvent or an organic oil, or an aqueous solution containing a third polymer, wherein the first two polymers are not soluble in the third solution. The mixture is stirred to form an emulsion of the first two polymers in the third continuous phase, and the solvent is slowly evaporated, creating microspheres with an inner core of the first polymer and an outer layer of the second polymer. In another embodiment, the rate of evaporation may be accelerated if necessary to promote the formation of the outer layer of the second polymer and then the core of the first polymer.

In another embodiment, after phase separation has occurred, one polymer may be formed within a layer of the other polymer by decreasing the temperature thus allowing one of the polymers to gel first and by further cooling to cause the second polymer to gel. In this embodiment, there may be no requirement for water removal from the microcapsules. Additionally, the polymers may be provided with crosslinkable groups, and the polymers may gel by the addition of a crosslinking agent. No evaporation of solvent is required in this case. In still another embodiment, the first polymer core may be formed within the second polymer layer, and then the solvent can be evaporated by spray drying or lyophilization.

A. Removal of Solvent by Evaporation

In one embodiment, a solvent evaporation technique may be used to make polymeric microspheres. In this embodiment, two polymers are dissolved in an aqueous solvent in which each polymer is soluble, at concentrations slightly above or at the cloud point of the two polymer solution. The resulting solution or suspension of the two polymers in solvent is then added to an organic or aqueous solution containing a different polymer that forces the first two polymers to phase separate, wherein the different polymer will not be part of the final product and is used only as a phase inducer, creating solid microspheres as the solvent evaporates. As the polymers become more concentrated, they begin to phase separate and if given enough time will configure themselves in their most thermodynamically stable configuration as dictated by the spreading coefficient theory described above. When the rate of solvent removal is increased, kinetic factors determine the extent of spreading, often trapping the spheres in a non-equilibrium configuration.

Due to the competing thermodynamics and kinetic processes, double-walled microspheres can be formed by two mechanisms. The first route involves a two polymer solution for which complete engulfment is predicted by the spreading coefficient theory and the rate of polymer precipitation is slow enough for this thermodynamic equilibrium to be reached. In the second method, the completely engulfed configuration is a transient intermediate of the two polymers as they approach thermodynamic equilibrium, and the rate of polymer precipitation is adjusted so as to trap the two polymers in this non-equilibrium configuration. Under certain conditions, the water phase need not be removed, particularly in embodiments involving cell encapsulation.

To form polymeric multiwall microcapsules, the aqueous solution of the two polymers is suspended in a non-solvent, preferably an organic solvent or an aqueous solution containing a substance that will cause the polymers in the polymer solution to phase separate from the polymeric solution. Between about 0 and 50% by volume of the second solution of a surface active agent also may be added, such as a surfactant or an emulsifier. The solvent(s) then are slowly evaporated. Vacuum evaporation, lyophilization, or solvent evaporation in a non-solvent can be employed, as well as other methods known to those skilled in the art. Temperatures less than 100° C. are preferred due to the labile nature of many biological active drugs. The polymer suspension can be frozen after one polymer has engulfed the other to stabilize the microspheres during solvent removal.

It is critical to control the rate of solvent removal, as well as the parameters previously discussed, for one polymer solution to form a layer around a core of another polymer solution and to produce uniform layers. However, the effect of the rate of solvent removal on polymer layer formation may be used advantageously to modify the final product. For example, increasing the rate of solvent removal causes the formation of spheres of the first polymer within the second polymer layer. The inclusion of the spheres can be useful in forming "channels" of one polymer within the other. By increasing the rate of evaporation still further, no inner layer is formed and all of the first polymer is present in spherical form within the second polymer layer. Inclusion of the spheres may be useful in forming "channels" of a biodegradable polymer such as zein, bovine serum (BSA), human serum albumin (HSA), and PEG-PLGA within an outer layer of a non-degradable polymer such as polyethylene glycol (PEG).

Removal of Solvent by Spray Drying

The microspheres also may be formed by spray drying a polymer solution containing the substance to be incorporated. It is important to dry the spheres slowly enough for the engulfmg polymer to completely coat the polymer with the higher surface tension.

Cooling of Mixtures of Melted Polymers.

Multilayer microspheres can be formed when two melted polymers which have a positive spreading coefficient are emulsified in a non-solvent and then are rapidly cooled. The rate of cooling is important to the formation of microspheres having complete, uniform layers of polymer.

Crosslinking Polymers Forming One or Both Polymer Layers

Polymers may be utilized which are hydrophilic and also contain crosslinkable groups, such as functional groups that can be ionically or covalently crosslinked. When using these polymers, it may not be necessary to evaporate the polymer solvent before the polymers are crosslinked. In this embodiment, the two polymers in solution are phase separated so that one polmer layer engulfs the other, and then one or both of the polymer layers are crosslinked.

Hydroxyl, carboxylic acid and amine groups can be crosslinked using metal ions, as known to those skilled in the art. In the preferred embodiment, hydrolytically stable poly (organophosphazenes) such as poly(carboxylatophenoxy) phosphazene and its copolymers, poly(acrylic acid), poly (methacrylic acid) or methacrylic acid copolymers, that contain carboxylic acid, sulfonic acid or hydroxyl substituent groups, or alginate or chitosan, are crosslinked with divalent or trivalent cations such as calcium, lead, lanthanum, bismuth, barium, magnesium, aluminum, copper, cobalt, nickel, chromium, or cadmium, and, in a preferred embodiment, zinc. In one embodiment, pharmaceutically acceptable cations may be utilized.

Covalent linkages between amine groups can be formed using a coupling agent such as glutaraldehyde, or by using a diacid chloride.

The polymers can also have free-radical polymerizable functional groups. An example of a free-radical polymerizable group is a carbon-carbon double bond. Preferred polymerizable regions are acrylates, diacrylates, oligoacrylates, dimethacrylates, oligomethoacrylates, or other biologically acceptable photopolymerizable groups. These groups can be polymerized using free-radical initiators such as azo-bis-isobutyronitrile (AIBN) and t-butyl peroxide, photoinitiators useful in the UV region (wavelengths below 380 nm) such as benzoin ethyl ether, and photoinitiators that are useful in the visible region (approximately 380 to 800 nm) such as certain dyes and chemical compounds known to those skilled in the art.

Useful photoinitiators are those which can be used to initiate polymerization of polymers by free-radical generation without cytotoxicity and within a short time frame, minutes at most and most preferably seconds. Initiators of choice for long wavelength ultraviolet (LWUV) initiation are dyes such as ethyl eosin, 2,2-dimethoxy-2-phenyl acetophenone, other acetophenone derivatives, and camphorquinone. Dyes also can be used in the visible region.

Light absorption by a dye causes the dye to assume a triplet state, the triplet state subsequently reacting with an amine to form a free radical which initiates polymerization. Preferred dyes include eosin dye and initiators such as 2,2-dimethyl-2-phenylacetophenone, 2-methoxy-2-phenylacetophenone, and camphorquinone.

Microsphere Formation by Gelation of Individual Phases.

By taking advantage of the individual properties of polymers, it is possible to induce gelation and solidification of the individual layers following phase separation and engulfment. One property that can be exploited is temperature-dependent gelation. Many naturally-occurring hydrophilic polymers such as gelatin, albumin and agarose gel when the temperature of concentrated solutions is lowered. The gelling temperature of agarose and gelatin is in the range of 26-40° C. depending on the source and formulation, while albumin solutions solidify below 15° C. Hydrophobic derivatives of some synthetic polymers, such as isopropylacrylamide, also exhibit temperature-dependent solution properties, with gel points in the range of 20–60° C. depending on the degree of hydrophobic substitution and concentration.

Another thermal property of protein-based polymers, namely denaturation or coagulation, can be used to solidify layers of a multi-walled sphere. When concentrated solutions of albumin, casein or zein are heated above 80° C., the proteins denature, changing their quarternary structure, and solidify. This property has been used to make single-walled microspheres of bovine serum albumin and zein.

Additionally, the thermal gelation or coagulation properties of one polymer can be combined with the ionic (or other) gelation properties of another polymer. Alginate, as an example, can be crosslinked with divalent or trivalent cations. Concentrated solutions of agarose (heated above the gelation point) can be mixed with alginate, and phase separation can be induced by the cooling of agarose and gelation of alginate with metal ions.

Formation of Additional Polymer Layers

Additional polymers can be layered using the above techniques, however, the complexity of the process dramatically increases with each additional polymer. It is therefore preferred to add other layers using methods known to those skilled in the art such as the hot-melt technique.

The present invention is further described by the following non-limiting examples.

EXAMPLE 1

Microcapsulates Prepared from Polyethylene Glycol and Dextran.

Figure 2:
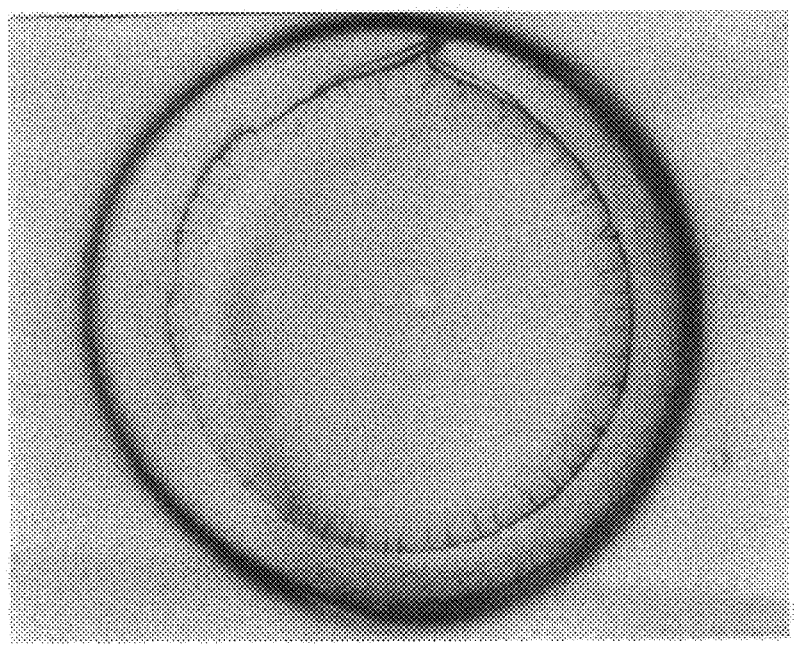
FIG. 2 is a light micrograph of a microsphere containing an inner core of polyethylene glycol and an outer core of dextran.
Figure 3:
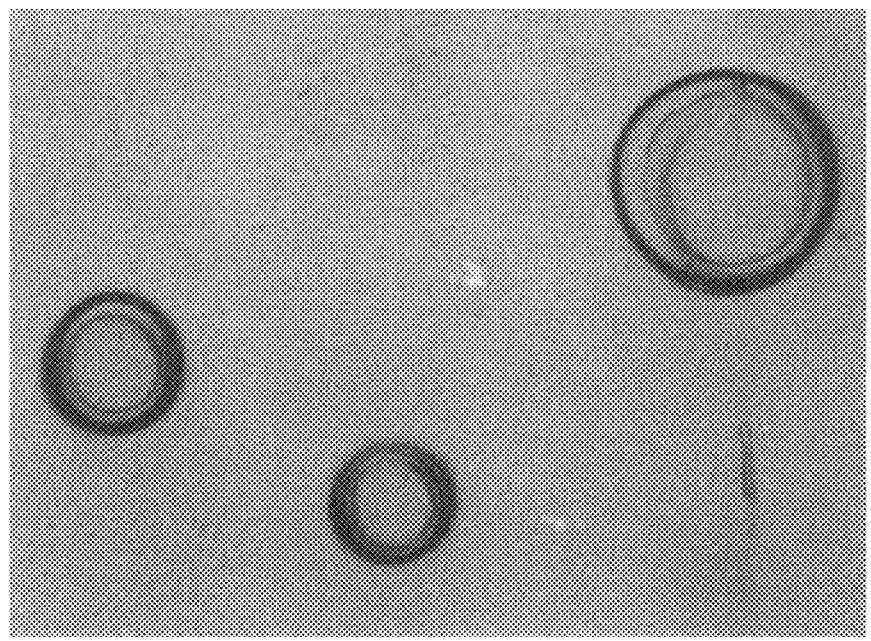
FIG. 3 is a light micrograph of several microspheres containing an inner core of polyethylene glycol and an outer core of dextran.

Polyethylene glycol (PEG, molecular weight 8,000 Da) and dextran (molecular weight 500,000 D) were used to form double-walled microspheres. Separate solutions of 30% PEG (w/v) and 20% dextran (w/v) were prepared and mixed together in equal volumes. A small quantity of Blue Dextran (molecular weight 2,000,000 Da) was included in the dextran solution to act as a visual tracer. The mixture was shaken to disperse the phases within each other. The solution was poured into 300 ml of mineral oil and stirred to form an emulsion. Stirring was continued for three days, during which time the solution was heated to 90° C. to expedite the evaporation of the aqueous solvent. Samples were removed periodically and observed using optical microscopy. Initially, the droplets showed distinct phase separation, with dextran as the outer layer (FIGS. 2 and 3). While over time some of the microspheres agglomerated, the double-walled nature of the spheres was retained. The hardened beads were recovered by decanting the mineral oil and washing the settled microspheres with ethanol.

EXAMPLE 2

Microspheres Prepared from Agarose and Gelatin

Figure 4:
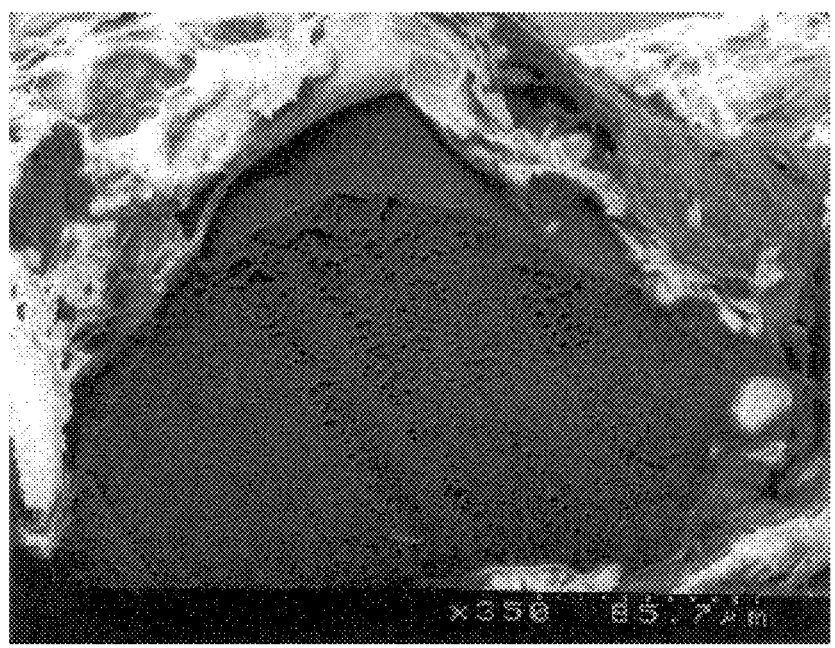
FIG. 4 is a scanning electron micrograph of a microsphere containing an outer core of gelatin and an inner core of agarose.

A similar method to Example 1 was used with agarose and gelatin as the polymers, however, in this case, the differences in gelation temperatures induced phase separation. Separate solutions of 20% agarose (w/v) and 4% gelatin (w/v) were prepared and maintained at 50° C. to keep the solutions in the liquid state. The solutions were mixed in equal volumes, dispersed by shaking and poured into 300 mL of mineral oil at 80° C. The mixture was stirred until the emulsion droplets were of an appropriate size range, then the oil bath was rapidly cooled to 4° C. The microspheres were collected by decanting the oil and were washed with ethanol. The spheres were analyzed with scanning electron microscopy (SEM) (FIG. 4). The inner core of these spheres consisted of agarose, which solidifies at 42° C., while the outer core consisted of gelatin which solidifies at 4° C.

Modifications and variations of the method of the present invention will be obvious to those skilled in the art from the foregoing detailed description and examples. One skilled in the art will also be able to optimize the method of the present invention for particular polymer and substance mixtures from the foregoing detailed description of the invention and examples. It is intended that such modifications, variations, and optimizations will come within the scope of the appended claims.

What is claimed is:

1. Polymeric microspheres formed of a first and second hydrophilic, water soluble polymer and a substance incorporated into at least one of the polymers;

wherein each microsphere includes an inner core of the first polymer and at least one distinct outer layer of the second polymer surrounding the inner core.

2. The polymeric microspheres of claim 1 wherein the first and second polymers are selected from the group consisting of polyamines, natural and synthetic polysaccharides, poly(oxalkylene)oxides, polyacrylamides and synthetic copolymers of hydrophilic and hydrophobic polymers.

3. The polymeric microspheres of claim 1 wherein the first and second polymers each are biodegradable polyelectrolytes.

4. The polymeric microspheres of claim 1 wherein the polymers are biodegradable and wherein the substance is a biologically active agent.

5. Polymeric microspheres formed of a first and second hydrophilic, water soluble polymer and a substance incorporated into at least one of the polymers;

wherein each microsphere includes a plurality of spheres of the first polymer and at least one distinct outer layer of the second polymer surrounding the spheres.

6. The polymeric microspheres of claim 1 wherein the substance is incorporated in both layers.

7. The polymeric microspheres of claim 1 wherein at least one of the polymers is in the form of a gel.

* * * * *